(12) United States Patent
Müller et al.

(10) Patent No.: US 6,306,589 B1
(45) Date of Patent: *Oct. 23, 2001

(54) BIOLOGICAL ASSAYS FOR ANALYTE DETECTION

(75) Inventors: Uwe Richard Müller, Plano; Diping Che, Westmont; Yijia Bao, Naperville, all of IL (US)

(73) Assignee: Vysis, Inc., Downers Grove, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/085,625

(22) Filed: May 27, 1998

(51) Int. Cl.[7] .............................. C12Q 1/68; C12N 1/00; G01N 21/64
(52) U.S. Cl. ................ 435/6; 435/243; 435/288.3; 435/288.7; 536/25.4; 250/461.2
(58) Field of Search ................ 435/6, 243; 536/25.4

(56) References Cited

U.S. PATENT DOCUMENTS

| | | | |
|---|---|---|---|
| 4,738,927 | * | 4/1988 | Taniguchi et al. .................. 435/243 |
| 4,908,307 | * | 3/1990 | Rodland ................................... 435/6 |
| 5,552,272 | * | 9/1996 | Bogart ..................................... 435/6 |
| 5,610,291 | * | 3/1997 | Woodard et al. .................... 536/25.4 |
| 5,942,397 | | 8/1999 | Tarlov et al. ............................ 435/6 |

FOREIGN PATENT DOCUMENTS

| | | |
|---|---|---|
| 0391608 | 10/1990 | (EP). |
| 0811693 | 12/1997 | (EP). |
| 0872733 | 10/1998 | (EP). |
| 0882980 | 12/1998 | (EP). |
| WO 91/18292 | 11/1991 | (WO). |
| WO 92/14136 | 8/1992 | (WO). |
| WO 96/17958 | 6/1996 | (WO). |

OTHER PUBLICATIONS

Search Report, EP 99 30 3931, Feb. 3, 2000.

* cited by examiner

Primary Examiner—Stephanie W. Zitomer
Assistant Examiner—Arun Chakrabarti
(74) Attorney, Agent, or Firm—Norval B. Galloway

(57) ABSTRACT

Fluorescence-based assay methods for detecting biological analytes in a sample. The fluorescence background in these methods is significantly lower than in conventional assay methods. Also provided are methods of attaching nucleic acids to a metallic or metalloid surface.

31 Claims, 2 Drawing Sheets

BIOLOGICAL ASSAYS FOR ANALYTE DETECTION

FIELD OF THE INVENTION

The invention relates to biological methods of assaying analytes.

BACKGROUND OF THE INVENTION

Biological assays for analyte detection generally involve attaching to the analyte (e.g., nucleic acids, proteins, hormones, lipids, or cells) a signal-generating moiety. Fluorescence-based bioassays require the detection of weak fluorescence signals. In a typical assay, the analyte is deposited onto a solid substrate such as a microscope slide or a glass chip. After undergoing biochemical treatment and fluorescent staining, the slide is examined with an optical instrument such as a fluorescence microscope. Light of certain wavelengths is applied to the slide, and the fluorescent emission from the deposited biomaterial is collected as a signal.

Transparent soda-lime and borosilicate glasses are commonly used as substrates to support fluorescently labeled samples. However, many of these materials exhibit significant autofluorescence, have finite absorbance, and can produce fluorescent emission throughout the visible region. A typical soda-lime glass slide can produce background fluorescence equivalent to a layer of a commonly used fluorescent dye with a surface density of more than $1 \times 10^9$ fluorophors/cm$^2$. This background fluorescence along with noise from other sources, such as stray light and Rayleigh and Raman scattering, can obscure the detection of weak fluorescent signals from the analyte, limiting the sensitivity of the assay.

Further, in many fluorescent assays for nucleic acid detection, nucleic acids are attached to a solid support via chemical linkers. Such linkers often are autofluorescent and can introduce background fluorescence.

SUMMARY OF THE INVENTION

The invention features improvements in biological assays. In one aspect, the invention features fluorescence-based assays that have a significantly reduced signal background compared to conventional assays. These assays include the steps of: (i) providing an opaque glass support with a surface that is in contact with a sample containing an analyte (e.g., a protein, a nucleic acid, a polysaccharide, a lipid, or a cell), where the analyte, in present in the sample, is labeled with a fluorochrome; (ii) illuminating the surface with light at a wavelength that excites the fluorochrome; and (iii) detecting fluorescent emission from the surface as an indication for the presence of the compound in the sample. As used herein, "an opaque glass support" refers to a glass support that is impervious to the excitation and emission lights of the fluorochrome used in an assay.

In the above assays, a reflective surface can be used in lieu of an opaque glass support. By "a reflective surface" is meant that, when incoming light is directed to the surface perpendicularly, the surface reflects at least about 15% (e.g., at least 25%, 50%, 75%, or 90%) of the incoming light, while transmitting no more than 20% (e.g., no more than 10%, 5%, or 1%) of the light. In assays using a reflective surface, the excitation light can be directed to the surface at an angle, i.e., non-perpendicularly. A reflective surface can be, for instance, metallic (e.g., chromium or aluminum) surface or metalloid (e.g., silicon) surface.

In the fluorescence assays of the invention, the analyte can be bound to the surface via a capture probe that binds specifically to the analyte and is immobilized on the surface.

In another aspect, the invention features methods of efficiently attaching nucleic acid to a metallic or metalloid surface. These methods include the steps of: (i) providing a solution that contains the desired nucleic acid; (ii) denaturing the nucleic acid in the solution; (iii) applying the solution to the metallic (e.g., chromium or aluminum) or metalloid (e.g., silicon) surface; and (iv) allowing the solution to dry on the surface, thereby attaching the nucleic acid to the surface. In these methods, the nucleic acid can be denatured in an alkaline solution (e.g., a NaOH solution) that has a pH of at least about 11, or by being heated to a temperature and for a time sufficient to denature the nucleic acid. A microscopy mounting medium, e.g., Gel/Mount™ (Biomeda Corp., Foster City, Calif.), can be optionally applied to the metal or metalloid surface to enhance the attachment of the nucleic acid to the surface.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can be used in the practice or testing of the present invention. All publications and any other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

DETAILED DESCRIPTION

The invention features (i) improved fluorescence-based bioassay methods in which background fluorescence is significantly reduced as compared to conventional methods, and (ii) improved methods for attaching nucleic acids to solid supports.

Methods of Reducing Fluorescence Background

Fluorescently labeled analytes are detected on a substrate (e.g., black glass) that is opaque in the wavelength regions where the fluorescent label absorbs and emits. Due to opaqueness of the substrate, penetration of the excitation light into the substrate and any returning fluorescence is substantially reduced. Rayleigh and Raman scattering from the interior of the substrate will also be prevented. Further, contamination and dust particles on the side and back surfaces of the substrate, which can generate background of much higher intensity than the real signal, will not be detected. Background originating stray light from below the substrate is also reduced or eliminated. Consequently, the background noise from this type of substrate is significantly lower than that from a conventional substrate (e.g., soda-lime glass).

The substrate is preferably non-fluorescent or has low autofluorescence. The chemical and physical properties of the substrate material should also be compatible with the assay. Suitable materials include, but are not limited to, colored or opaque glasses and opaque, plastic-based materials. Exemplary colored glasses are Schott M-UG-2, M-UG-6, UG-1, UG-11, ND, RG715, RG9, RG780, ND-1, and ND-10 (Germany); and Corning 2030, 2540, 2550, 2600, 5840, 5860, 5874, and 9863. The substrate can be fabricated into forms such as slides, wafers, or chips.

Alternatively, the analyte-receiving surface of the substrate is reflective, and can be, for example, a surface of a solid support coated with a metalloid or metallic thin film, or a polyshed surface of a metal or metalloid plate. The reflective surface eliminates the transmission of excitation and fluorescent emission through the substrate if the substrate is otherwise transparent to the excitation and emission light. By illuminating the surface at an appropriate angle, excitation light is reflected away from the collection optics, eliminating autofluorescence from the collection optics; consequently, less efficient filters can be used to absorb autofluorescence.

A variety of reflective coatings can be used, as long as the chemical and physical properties of the coating material is compatible with the assay and efficient attachment of an analyte can be achieved. Suitable substrates include, but are not limited to, coated glass materials used in glass lithography, e.g., chromium-coated glass available from Nanofilm (Westlake Village, Calif.).

Figure 1:
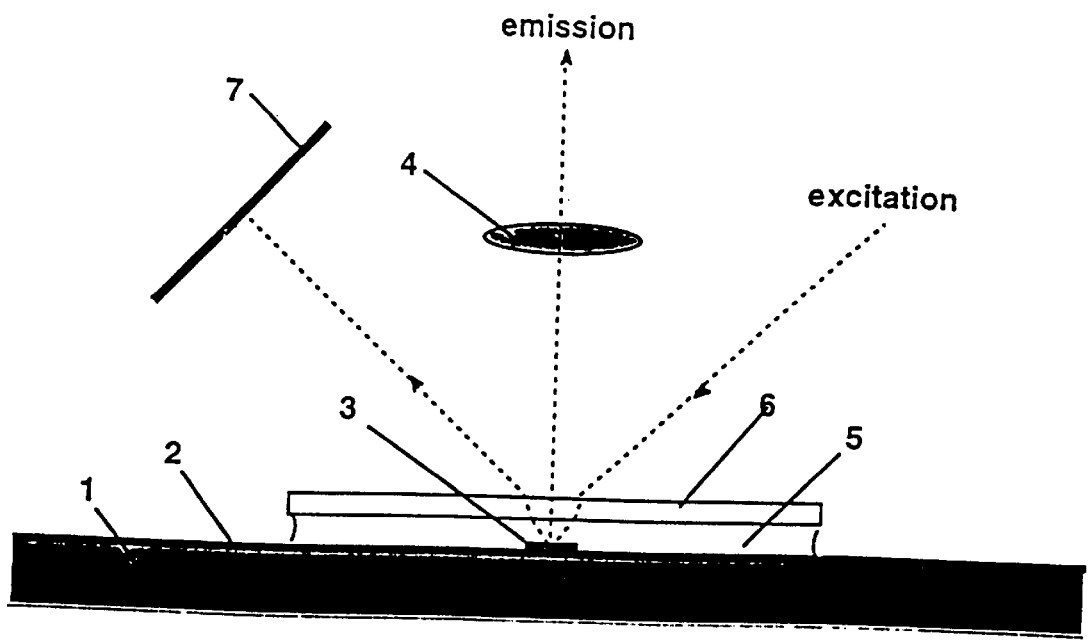
FIG. 1 is a diagram illustrating a fluorescence-based assay in which a chromium-coated soda-lime glass slide is used as a support for analyte DNA.

FIG. 1 shows a substrate 1 formed in the shape of a conventional microscope slide with a smooth surface coated with a thin chromium film 2. Fluorescently labeled DNA fragments 3 are deposited onto the surface either randomly or addressably in an array. After biochemical treatments of the deposited molecules, a liquid media 5 that provides proper pH is optionally applied onto the slide and covered with a thin coverslip 6. The liquid media can optionally contain an antifade reagent, which is a composition that prevents oxidation of a fluorochrome. An exemplary antifade reagent is p-phenylenediamine, available from Aldrich Chem., Co. (Milwaukee, Wis.). The liquid media can also contain a counterstain, e.g., 4',6-diamidino-2-phylindole ("DAPI"). The slide is then examined with a fluorescence imaging system, in which excitation light illuminates the chromium-coated side of the slide. The collection optics for fluorescent emission 4 is positioned directly above the illuminated surface, with the optical axis perpendicular to the coated surface. Such a position allows for reflection of fluorescent light into the collection optics, approximately doubling the intensity of the fluorescent signal detected by the optics. The excitation light is applied in an angle such that the reflected beam does not enter the collection optics. A mirror 7 can also be used to enhance the intensity of the excitation light.

The new methods can be used in a variety of fluorescence assays such as fluorescence immunoassays, fluorescence in situ hybridization, comparative genomic hybridization ("CGH"), genosensor-based CGH ("gCGH"; see, e.g., Kallioniemi et al., Science, 258:818–821, 1992), molecular lawn (see U.S. patent application Ser. Nos. 08/768,177 and 08/991,675), or general DNA chip based assays (see, e.g., U.S. Pat. Nos. 5,445,934, 5,510,270, and 5,556,752).

Well established methods can be used to attach analyte nucleic acids, or capture probes specific for analyte nucleic acids, to glass or metallic coated surfaces. See, e.g., Joos et al., Analytical Biochemistry, 247: 96–101, 1997; Maskos et al., Nucleic Acids Research, 20: 1679–1684, 1992; Fodor et al., Science, 251: 767–773, 1991; Lowe, Chemical Society Reviews, 24: 309–317, 1995; Guo et al., Nucleic Acids Research, 22: 5646–5465, 1994; and Bischoff, Analytical Biochemistry, 164: 336–344, 1987. Attachment methods that work for glass surfaces also work well for silicon substrates. To do this, the silicon substrate is heated to oxidize the surface layer so that the surface has the same chemical properties as a glass slide.

To attach a nucleic acid to a metallic surface, the surface can be treated with a first silane compound (e.g., Gelest's WAS 7021 (Tullytown, Pa.)) and then with a second silane compound (e.g., (3-Glycidoxypropyl)-Trimethoxysilane). The first silane coating binds to the metallic surface, and the second silane coating provides a reactive group (e.g., an epoxy group) for attachment of an appropriately modified nucleic acid (e.g., an aminated nucleic acid). Preferably, these two silane coatings are transparent in the wavelength regions that are most often used.

Analyte proteins (e.g., cell surface proteins) can be attached to a solid support by any of a number of standard methods, including direct adsorption or chemical coupling to reactive groups on the surface. For example, a solid surface can be derivatized to generate active amine groups; then an amine- and sulfhydryl-reactive heterobifunctional crosslinker (e.g., succinimidyl-4-(N-maleimidomethyl) cyclohexane-1-carboxylate or other DOUBLE-AGENT™ crosslinkers available from Pierce, Rockford, Ill.) is used to link a free cysteine group in a polypeptide to the amine group on the solid surface. Homobifunctional crosslinkers can be used as well.

An analyte can be linked covalently or noncovalently (directly or indirectly) to a detectable label moiety such as a fluorochrome (e.g., fluorescein, phycoerythrin, Texas Red, or Allophycocyanin), or an enzyme that catalyzes a fluorescence reaction (e.g., horseradish peroxidase). By way of example, an analyte nucleic acid may be labeled with a probe that is attached to a fluorochrome; and an antigen can be labeled with a specific antibody conjugated to horseradish peroxidase.

The experiments described below illustrate several embodiments of the new fluorescence-based bioassays methods.

Quantitative determinations of signals emanating from fluorescently labeled compounds were carried out with a large field fluorescent imaging system developed at Vysis, Inc. (Downers Grove, Ill.). The imaging system consisted of a 450 W Xenon arc lamp (SLM Instruments Inc., Champaign Urbana, Ill.), a charge coupled device detector (CH200, Photometrics, Tucson, Ariz.), and a filter set (Chroma Technology, Brattleboro, Vt.) for three commonly used fluorescent dyes—DAPI for blue, fluorescein isothiocyanate ("FITC") for green, and Texas red ("TRED") for red. The imaging system was controlled by a Power Macintosh 7100/80 with an imaging acquisition/analysis software (IpLab, Signal Analytics, Corp., Vienna, Va.). The results are shown in Table 1.

TABLE 1

Relative Background Fluorescence

| Slide | Blue | Green | Red | Source |
| --- | --- | --- | --- | --- |
| Soda-lime glass | 1 | 1 | 1 | VWR Scientific products |
| Fused Silica | 0.43 | 0.38 | 0.59 | Haraeus Amersil (Duluth, GA) |
| M-UG-2 black glass | 0.11 | 0.08 | 0.16 | Schott Mainz (Germany) |
| M-UG-6 black glass | 0.10 | 0.08 | 0.18 | Schott Mainz (Germany) |
| Soda-lime with | 0.04 | 0.03 | 0.09 | Nanofilm |

TABLE 1-continued

| | Relative Background Fluorescence | | | |
|---|---|---|---|---|
| Slide | Blue | Green | Red | Source |
| Cr coating Soda-lime with Al coatinq | 0.05 | 0.03 | 0.09 | Nanofilm |
| Silicon | 0.26 | 0.06 | 0.13 | Nova Electronic Materials (Richardson, TX) |

Table 1 shows the relative background fluorescence of untreated materials scaled to the commonly used soda-lime microscope slide (VWR Scientific Products, West Chester, Pa.). The relative background fluorescence includes contributions from light scattering, stray light and filter imperfections, but all electronic noise has been subtracted. The results show that black glass slides and slides with metallic coatings offer 4 and 10 fold background reductions, respectively, over fused silica.

In another experiment, fluorescent intensity was measured on fluorescein-conjugated beads (Flow Cytometry Standards Corp., Hata Rey, PR) mixed with a commonly used antifade medium (Catalogue # 824–28, Flow Cytometry Standards Corp.) and sandwiched between a slide and a glass coverslip. Quantitative analysis of the images revealed that the overall background for the Cr-coated slide was only 21% of that for regular glass. The overall background included not only contributions from light scattering, stray light, and filter imperfections, but also autofluorescence from the mounting medium and the coverslip. Notably, the net signal intensity was doubled, due to reflection of incident light, passing through the fluorophors twice, and reflection of the fluorescent light, which would otherwise not enter the detection optics.

Another experiment demonstrates that the new fluorescence-based assay methods can be used to detect analyte DNA complexes. In this experiment, the slide materials listed in Table 1 were used as array supports (i.e., chips) in genosensor-based comparative genomic hybridization ("gCGH"). The gCGH technology was developed to improve on standard CGH, where DNA from a sample tissue is labeled with one fluorophor (e.g., TRED), mixed with an equal amount of reference DNA labeled with a different fluorophor (e.g., FITC), and then co-hybridized to metaphase chromosomes that are affixed to microscope slides. In gCGH, cloned DNA fragments immobilized on the chip surface in an array format are used in lieu of metaphase chromosomes. After hybridization, the target spots are washed and counter-stained with DAPI, which stains all DNA blue. The slide is then analyzed with a multi-color fluorescence imaging system. Image analysis software determines the presence of a target spot by the DAPI fluorescence, and then determines the relative amount of sample and reference DNA hybridization by measuring the red to green fluorescence ratio.

Cr-coated glass slides were made from Cr-coated glass obtained from Nanofilm. The following steps were carried out to prepare the metallic surface for DNA attachment. These steps are also applicable to other metallic surfaces such as Al-coated surfaces. Briefly, the metallic surface was treated with a 2% water-based solution of silesquioxane oligomers (Gelest, Inc.) for 10 minutes at room temperature, and washed with water. Silanization was then carried out with a 5% solution of glycidoxypropyl-trimethoxysilane ("GPTS"; Gelest, Inc.) in water at room temperature for 2 hours. Aminated DNA was then attached to the treated surface by reaction of the primary amine with the epoxy group.

DNA extracted from COLO 320 (American Type Culture Collection ("ATCC") # CCL-220) or HTB-18 (ATCC # HTB-18) cells under standard conditions were used in the experiment. The hybridization mixture contained, in 20 $\mu$l, 200 ng of human reference DNA (i.e., human blood DNA) probes labeled with Spectrum Red, 200 ng of test DNA probes (derived from COLO 320 or HTB-18 cells) labeled with Spectrum Green, 2×SSC, 10% dextran sulfate, 1 $\mu$g/$\mu$l Cot1 DNA, 1 $\mu$g/$\mu$l salmon sperm DNA, and 5×Denhardts solution. The mixture was incubated for 4 hours at 37° C. before being added to the chips onto which the target DNA had been immobilized.

Hybridization on the chips was carried out overnight at 37° C. The chips were washed with 2×SSC at room temperature for 5 minutes, with 2×SSC and 50% formamide at 40°C. for 30 minutes, and then with 2×SSC at room temperature for 10 minutes. Subsequently, the chips were dried at room temperature in the dark. Before imaging, 10 $\mu$l of GEL/MOUNT™ was placed onto the chip in the area of the array, which was then covered with a coverslip. For imaging, the chromium chip was imaged with an integration time of 20 seconds. For comparison, DNA was attached to a soda-lime glass chip (i.e., a microscope slide) via standard epoxysilane chemistry and hybridized under identical conditions; and the glass chip was imaged for 10 seconds. The results showed that more than 4-fold reduction in overall background was achieved with Cr-coated slides. Similar results were obtained with dark glass slides, silicon slides and Al-coated slides.

An advantage of using the Cr-coated surface is that if an appropriate hybridization fluid, it is very easy to remove unbound probe from the chip surface due to the hydrophobic properties of chromium. An appropriate hybridization fluid can be one that does not contain a detergent capable of altering the hybrophobic property of the chromium surface. As a result, the fluorescent background due to non-specific binding of probe is lessened or even eliminated. The hybridization efficiency may also be increased, since less non-specific binding allows for increased probe availability for specific binding.

Methods of Attaching Nucleotide Acids to Substrates

The invention provides a fast and surprisingly simple and convenient method for attaching nucleic acids to a solid surface. In the new attachment methods, nucleic acids are bound noncovalently to a substrate surface, e.g., a metallic or metalloid surface. To accomplish this, a solution containing denatured nucleic acid is applied to a substrate and allowed to dry at room temperature or in an oven. The nucleic acid can be denatured by raising the pH of the solution to a level of about 11.0 or higher. High pH in a solution can be achieved by use of a variety of alkaline materials, e.g., an alkali metal or alkaline earth metal hydroxide such as NaOH, KOH and the like.

Alternatively, the nucleic acids can be denatured by heat, e.g., by heating a solution containing the nucleic acids at 95° C. or higher for 2 to 5 minutes. The solution containing the denatured nucleic acids is then applied to a metallic or metalloid surface and allowed to dry.

It is believed that the electrostatic forces present in the denatured, single-stranded nucleic acids are typically adequate for effective attachment to the substrate. The above processes work particularly well for long polynucleotides (e.g., more than about 550 nucleotides ("nt") in length).

To improve attachment of polynucleotides that are less than about 550 nt in length), the nucleic acids spotted to a substrate surface can be treated with a microscopy mounting medium such as GEL/MOUNT™ or an equivalent of GEL/MOUNT™. While not wishing to be bound by any specific theory, it is believed that GEL/MOUNT™, which contains polymeric molecules, acts as a volume displacement reagent, bringing nucleic acids to closer proximity to the substrate surface. Alternatively, this mounting reagent may allow the nucleic acids to be in closer contact with each other, thereby promoting formation of a nucleic acid network that traps nucleic acids not directly attached to the substrate surface. Any reagent that has similar effects on nucleic acid can be used.

The conventional nucleic acid attachment methods are known to introduce background fluorescence due to the fact that most chemical linkers are autofluorescent. By eliminating the use of such linkers, the new attachment methods circumvent this problem.

In one example, 0.9 $\mu g/\mu l$ unmodified and undigested plasmid DNA (6 kb) in water or 100 mM NaOH was manually spotted onto untreated Cr-coated chips and allowed to dry. After a wash with 2×SSC, the DNA was stained with GEL/MOUNT™/DAPI and examined for DAPI fluorescent signals. The results showed that the spots of undenatured DNA, i.e., DNA in water, were washed out; in contrast, the spots of denatured DNA, i.e., NaOH-treated DNA, bound well, with similar DAPI intensity to 49 kb long lambda DNA spots generated under NaOH denaturation conditions. Specific hybridization to the attached DNA was observed using nick translated plasmid probe under standard hybridization and wash conditions.

To test whether the alkaline method described above works well for attachment of short DNA molecules, NaOH-treated, sonicated lambda DNA, which was about 500 nt long on average, were spotted to Cr-coated chips as described herein. Subsequent to washing with 2×SSC, the spotted DNA was stained with GEL/MOUNT™/DAPI and examined for fluorescent signal. The results showed that the DNA remained attached to the chips even after the wash.

These results demonstrate that binding of DNA to a Cr- or Al-coated surface achieved by the new method endures the harsh conditions of hybridization and wash steps as well as the binding achieved by the conventional covalent methods.

In another example, the effect of GEL/MOUNT™ treatment on DNA attachment and hybridization was tested. Sonicated lambda DNA of various lengths (i.e., 48 kb, 2.5 kb, 900 nt, 550 nt, 400 nt, and 300 nt, respectively) were used in the experiment.

Figure 2:
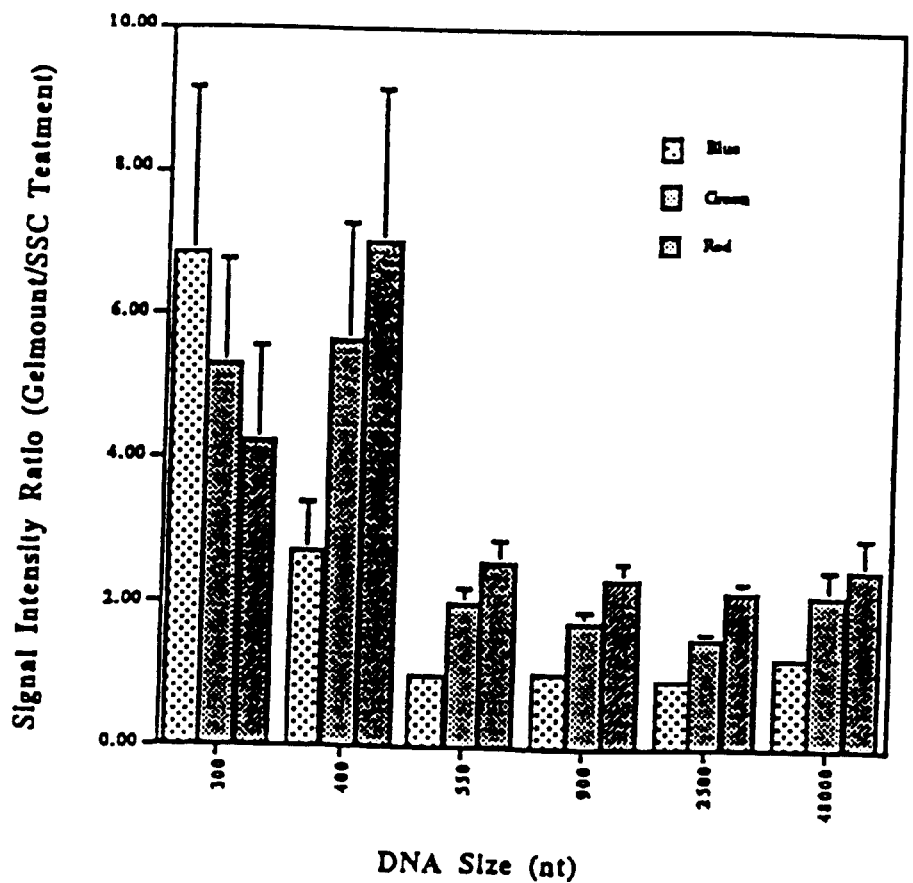
FIG. 2 is a graph showing that treatment with GEL/MOUNT™ (a permanent aqueous mounting medium available from Biomeda Corp., Foster City, Calif.) improves the attachment of DNA, especially short DNA, to a chromium chip. The Y axis represents the ratio of the signal from a DNA spot treated with GEL/MOUNT™ to the signal from a control DNA spot treated with 2×SSC.

The sonicated DNA was suspended in 100 mM NaOH and attached onto an untreated chromium chip as described above. Fifteen $\mu l$ of GEL/MOUNT™ were then added to the DNA chips, and incubated at room temperature for 1 hour. The chips were washed with 2×SSC and stained with DAPI. The data shown in FIG. 2 demonstrates that the GEL/MOUNT treatment significantly improves the attachment of DNA, especially short DNA (e.g., about 300 to 400 nt in length), to the chromium chip. For instance, the blue DAPI signal from the GEL/MOUNT™-treated 300 nt spots was found to be 7 fold higher than that from the corresponding SSC-treated spots.

To examine the effect of GEL/MOUNT™ on hybridization, the DNA chips were incubated with 20 ng of Spectrum green labeled lambda DNA and 20 ng of Spectrum red labeled lambda DNA. For the spots containing 300 nt or 400 nt long target DNA, the fluorescent signals of the GEL/MOUNT™-treated chips were 4 to 7 fold higher than those of untreated chips

Other Embodiments

It is to be understood that while the invention has been described in conjunction with the detailed description thereof, the foregoing description is intended to illustrate and not to limit the scope of the invention, which is defined by the scope of the appended claims.

Other aspects, advantages, and modifications are within the scope of the following claims.

What is claimed is:

1. A method of detecting a polynucleotide analyte in a sample, the method comprising:

providing a reflective surface that is in contact with the sample;

immobilizing the polynucleotide analyte on the reflective surface without chemical linkers interposed between the reflective surface and the polynucleotide analyte, wherein the polynucleotide analyte is labeled with a fluorochrome;

illuminating the surface with light at a wavelength that excites the fluorochrome; and detecting fluorescent emission from the surface as an indication of the presence of the polynucleotide analyte in the sample.

2. The method of claim 1, wherein the analyte is bound to the reflective surface via a capture probe that binds specifically to the analyte and is immobilized on the surface.

3. The method of claim 1, wherein the reflective surface is a metallic or metalloid surface.

4. The method of claim 3, wherein the metallic surface is a chromium surface.

5. The method of claim 3, wherein the metallic surface is an aluminum surface.

6. The method of claim 3, wherein the metalloid surface is a silicon surface.

7. A method of attaching a polynucleotide to a metallic or metalloid surface, the method comprising:

providing a solution that contains the polynucleotide;

denaturing the polynucleotide in the solution;

applying the solution directly to the metallic or metalloid surface; and allowing the solution to dry on the surface, thereby attaching the polynucleotide to the surface.

8. The method of claim 7, wherein the solution has a pH of at least about 11.

9. The method of claim 8, wherein the solution comprises sodium hydroxide.

10. The method of claim 7, wherein the polynucleotide is denatured by heating the solution to a temperature and for a time sufficient to denature the polynucleotide.

11. The method of claim 7, wherein the metallic surface is a chromium surface.

12. The method of claim 7, wherein the metallic surface is an aluminum surface.

13. The method of claim 7, wherein the metalloid surface is a silicon surface.

14. The method of claim 1, wherein the excitation light is directed to the surface at an angle.

15. A method of detecting a polynucleotide analyte in a sample, the method comprising:

providing a metallic or metalloid surface to which a capture polynucleotide has been attached according to the method of claim 7;

contacting the metallic or metalloid surface with the sample, wherein the polynucleotide analyte, if present in the sample, is labelled with a fluorochrome;

illuminating the surface with a light at a wavelength that excites the fluorochrome; and detecting fluorescent emission from the surface as an indication of the presence of the polynucleotide analyte in the sample.

16. The method of claim 15, wherein the metallic surface is a chromium surface.

17. The method of claim 15, wherein the metallic surface is an aluminum surface.

18. The method of claim 15, wherein the metalloid surface is a silicon surface.

19. The method of claim 15, wherein the excitation light is directed to the surface at an angle.

20. A method of detecting an analyte in a sample, the method comprising:

providing a reflective surface;

immobilizing an analyte to the reflective surface by a noncovalent interaction between the analyte and the reflective surface;

labeling the analyte with a fluorochrome;

illuminating the reflective surface with a light at a wavelength that excites the fluorochrome; and detecting fluorescent emission from the surface as an indication of the presence of the analyte in the sample.

21. The method of claim 20, wherein the analyte is a polynucleotide.

22. The method of claim 20, wherein the reflective surface is a metallic or metalloid surface.

23. The method of claim 20, wherein the reflective surface is a chromium surface.

24. The method of claim 20, wherein the reflective surface is an aluminum surface.

25. The method of claim 20, wherein the reflective surface is a silicon surface.

26. A method of detecting a polynucleotide analyte in a sample, the method comprising:

providing a reflective surface;

immobilizing a capture probe to the reflective surface by a noncovalent interaction between the capture probe and the reflective surface;

bringing the sample into contact with the capture probe immobilized on the reflective surface;

labeling the polynucleotide analyte, if present in the sample, with a flurochrome;

illuminating the reflective surface with a light at a wavelength that excites the fluorochrome; and detecting fluorescent emission from the surface as an indication of the presence of the polynucleotide analyte in the sample.

27. The method of claim 26, wherein the capture probe is a polynucleotide.

28. The method of claim 26, wherein the reflective surface is a metallic or metalloid surface.

29. The method of claim 26, wherein the reflective surface is a chromium surface.

30. The method of claim 26, wherein the reflective surface is an aluminum surface.

31. The method of claim 26, wherein the reflective surface is a silicon surface.

* * * * *